(12) United States Patent
Davison et al.

(10) Patent No.: US 7,674,273 B2
(45) Date of Patent: Mar. 9, 2010

(54) METHOD FOR PERFORMING A SURGICAL PROCEDURE AND A CANNULA FOR USE IN PERFORMING THE SURGICAL PROCEDURE

(75) Inventors: Thomas W. Davison, North Attleboro, MA (US); Timothy E. Taylor, Hoover, AL (US); Adam Sher, North Attleboro, MA (US)

(73) Assignee: Zimmer Spine, Inc., Minneapolis, MN (US)

( * ) Notice: Subject to any disclaimer, the term of this patent is extended or adjusted under 35 U.S.C. 154(b) by 1450 days.

(21) Appl. No.: 10/958,505

(22) Filed: Oct. 5, 2004

(65) Prior Publication Data

US 2005/0043754 A1    Feb. 24, 2005

Related U.S. Application Data

(60) Division of application No. 10/435,730, filed on May 9, 2003, now Pat. No. 6,811,558, which is a division of application No. 09/772,605, filed on Jan. 30, 2001, now Pat. No. 6,800,084, which is a continuation-in-part of application No. 09/137,335, filed on Aug. 20, 1998, now Pat. No. 6,187,000.

(51) Int. Cl.
    *A61M 29/00* (2006.01)
(52) U.S. Cl. ............... 606/198; 604/104; 604/264
(58) Field of Classification Search .......... 606/108, 606/191, 198, 205–210, 127; 604/104, 105, 604/164.05, 264
    See application file for complete search history.

(56) References Cited

U.S. PATENT DOCUMENTS 1,170,324 A    2/1916    Pomerene 2,605,582 A *  8/1952    Allen ............... 43/100

(Continued)

FOREIGN PATENT DOCUMENTS

AU    A-13672/95    9/1995

(Continued)

OTHER PUBLICATIONS

"Arthroscopic Lumbar Intervertebral Fusion" by Kambin, Adult Spine: Principles and Practice, pp. 2037-2046 (1997).

(Continued)

*Primary Examiner*—Michael J Milano
*Assistant Examiner*—Victor X Nguyen
(74) *Attorney, Agent, or Firm*—Crompton, Seager & Tufte, LLC.

(57) ABSTRACT

A method of performing a surgical procedure on a body includes providing a cannula having a tubular structure with first and second tubular portions defining first and second passages for receiving surgical instruments. The second tubular portion is inserted inside the body and the first tubular portion is inserted so that the first tubular portion extends from an exterior of the body to inside the body. The second tubular portion expands to increase the cross-sectional area of the second passage in the second tubular portion while the second tubular portion is inside the body. The cross-sectional area of the first passage in the first tubular portion is maintained. The first tubular portion has a first thickness and the second tubular portion has a second thickness different than the first thickness.

24 Claims, 4 Drawing Sheets

U.S. PATENT DOCUMENTS

| | | | |
|---|---|---|---|
| 3,044,461 A | * | 7/1962 | Murdock .................... 600/208 |
| 3,503,398 A | | 3/1970 | Fogarty et al. |
| 3,789,852 A | | 2/1974 | Kim et al. |
| 3,841,317 A | | 10/1974 | Awais |
| 4,449,532 A | | 5/1984 | Storz |
| 4,451,256 A | | 5/1984 | Weikl et al. |
| 4,545,374 A | | 10/1985 | Jacobson |
| 4,573,448 A | | 3/1986 | Kambin |
| 4,601,713 A | | 7/1986 | Fuqua |
| 4,611,594 A | | 9/1986 | Grayhack et al. |
| 4,617,929 A | | 10/1986 | Gill et al. |
| 4,716,901 A | | 1/1988 | Jackson et al. |
| 4,817,587 A | | 4/1989 | Janese |
| 4,819,620 A | | 4/1989 | Okutsu |
| 4,863,133 A | | 9/1989 | Bonnell |
| 4,899,729 A | | 2/1990 | Gill et al. |
| 4,921,478 A | | 5/1990 | Solano et al. |
| 4,984,564 A | | 1/1991 | Yuen |
| 5,025,778 A | | 6/1991 | Silverstein et al. |
| 5,131,382 A | | 7/1992 | Meyer |
| 5,139,499 A | | 8/1992 | Small et al. |
| 5,139,511 A | | 8/1992 | Gill et al. |
| 5,163,949 A | | 11/1992 | Bonutti |
| 5,171,279 A | | 12/1992 | Mathews |
| 5,190,561 A | | 3/1993 | Graber |
| 5,195,541 A | | 3/1993 | Obenchain |
| 5,196,023 A | | 3/1993 | Martin |
| 5,197,971 A | | 3/1993 | Bonutti |
| 5,224,680 A | | 7/1993 | Greenstein et al. |
| 5,232,443 A | | 8/1993 | Leach |
| 5,279,564 A | | 1/1994 | Taylor |
| 5,287,845 A | | 2/1994 | Faul et al. |
| 5,295,994 A | | 3/1994 | Bonutti |
| 5,312,417 A | | 5/1994 | Wilk |
| 5,313,962 A | | 5/1994 | Obenchain |
| 5,345,927 A | | 9/1994 | Bonutti |
| 5,346,504 A | | 9/1994 | Ortiz et al. |
| 5,354,302 A | | 10/1994 | Ko |
| 5,370,647 A | * | 12/1994 | Graber et al. ............... 606/127 |
| 5,370,659 A | | 12/1994 | Sakashita |
| 5,395,317 A | | 3/1995 | Kambin |
| 5,417,203 A | | 5/1995 | Tovey et al. |
| 5,439,464 A | | 8/1995 | Shapiro |
| 5,443,479 A | | 8/1995 | Bressi, Jr. |
| 5,454,365 A | | 10/1995 | Bonutti |
| 5,472,426 A | | 12/1995 | Bonati et al. |
| 5,484,437 A | | 1/1996 | Michelson |
| 5,489,307 A | | 2/1996 | Kuslich et al. |
| 5,490,819 A | | 2/1996 | Nicholas et al. |
| 5,503,617 A | | 4/1996 | Jako |
| 5,520,607 A | | 5/1996 | Frassica et al. |
| 5,529,571 A | | 6/1996 | Daniel |
| 5,556,376 A | | 9/1996 | Yoon |
| 5,571,072 A | | 11/1996 | Kronner |
| 5,575,754 A | | 11/1996 | Konomura |
| 5,601,590 A | | 2/1997 | Bonutti et al. |
| 5,601,690 A | | 2/1997 | Gauld et al. |
| 5,643,282 A | | 7/1997 | Kieturakis |
| 5,649,902 A | | 7/1997 | Yoon et al. |
| 5,667,520 A | | 9/1997 | Bonutti |
| 5,690,606 A | | 11/1997 | Slotman |
| 5,707,359 A | * | 1/1998 | Bufalini ..................... 604/104 |
| 5,762,629 A | | 6/1998 | Kambin |
| 5,782,919 A | | 7/1998 | Zdeblick et al. |
| 5,792,044 A | | 8/1998 | Foley et al. |
| 5,795,289 A | | 8/1998 | Wyttenbach |
| 5,813,978 A | | 9/1998 | Jako |
| 5,817,062 A | | 10/1998 | Flom et al. |
| 5,827,319 A | | 10/1998 | Carlson et al. |
| 5,851,214 A | | 12/1998 | Larsen et al. |
| 5,865,802 A | | 2/1999 | Yoon et al. |
| 5,902,231 A | | 5/1999 | Foley et al. |
| 5,954,635 A | | 9/1999 | Foley et al. |
| 5,961,499 A | | 10/1999 | Bonutti et al. |
| 5,976,161 A | | 11/1999 | Kirsch et al. |
| 5,997,508 A | | 12/1999 | Lunn et al. |
| 6,036,638 A | | 3/2000 | Nwawka |
| 6,120,437 A | | 9/2000 | Yoon et al. |
| 6,126,671 A | | 10/2000 | Richards et al. |
| 6,152,871 A | | 11/2000 | Foley et al. |
| 6,162,236 A | | 12/2000 | Osada |
| 6,171,299 B1 | | 1/2001 | Bonutti |
| 6,175,758 B1 | | 1/2001 | Kambin |
| 6,187,000 B1 | | 2/2001 | Davison et al. |
| 6,254,628 B1 | | 7/2001 | Wallace et al. |
| 6,306,170 B2 | | 10/2001 | Ray |
| 6,312,443 B1 | | 11/2001 | Stone |
| 6,338,730 B1 | | 1/2002 | Bonutti et al. |
| 6,358,266 B1 | | 3/2002 | Bonutti |
| 6,361,488 B1 | | 3/2002 | Davison et al. |
| 6,371,968 B1 | | 4/2002 | Kogasaka |
| 6,383,195 B1 | | 5/2002 | Richard |
| 6,432,048 B1 | | 8/2002 | Francois |
| 6,494,893 B2 | | 12/2002 | Dubrul et al. |
| 6,497,654 B1 | | 12/2002 | Leonard et al. |
| 6,524,320 B2 | | 2/2003 | DiPoto |
| 6,530,880 B2 | | 3/2003 | Pagliuca |
| 6,530,926 B1 | | 3/2003 | Davison |
| 6,564,078 B1 | | 5/2003 | Marino et al. |
| 6,589,225 B2 | | 7/2003 | Orth et al. |
| 6,620,129 B2 | | 9/2003 | Stecker et al. |
| 6,648,888 B1 | | 11/2003 | Shluzas |
| 6,652,553 B2 | | 11/2003 | Davison et al. |
| 6,800,084 B2 | | 10/2004 | Davison et al. |
| 6,811,558 B2 | | 11/2004 | Davison et al. |
| 6,837,891 B2 | | 1/2005 | Davison et al. |
| 7,001,397 B2 | | 2/2006 | Davison et al. |
| 7,033,369 B2 | | 4/2006 | Davison et al. |
| 7,056,321 B2 | | 6/2006 | Pagliuca et al. |
| 7,108,705 B2 | | 9/2006 | Davison et al. |
| 7,144,393 B2 | | 12/2006 | DiPoto et al. |
| 2001/0011170 A1 | | 8/2001 | Davison et al. |
| 2001/0049498 A1 | | 12/2001 | Davison et al. |
| 2002/0002360 A1 | | 1/2002 | Orth et al. |
| 2003/0009130 A1 | | 1/2003 | Stecker et al. |
| 2003/0014068 A1 | | 1/2003 | Bonutti |
| 2003/0040656 A1 | | 2/2003 | Pagliuca et al. |
| 2003/0073998 A1 | | 4/2003 | Pagliuca et al. |
| 2003/0083688 A1 | | 5/2003 | Simonson |
| 2003/0083689 A1 | | 5/2003 | Simonson |
| 2003/0139648 A1 | | 7/2003 | Foley et al. |
| 2003/0153911 A1 | | 8/2003 | Shluzas |
| 2003/0153927 A1 | | 8/2003 | DiPoto et al. |
| 2003/0167058 A1 | | 9/2003 | Shluzas |
| 2003/0191371 A1 | | 10/2003 | Smith et al. |
| 2003/0195405 A1 | | 10/2003 | Marino et al. |
| 2003/0195493 A1 | | 10/2003 | Davison et al. |
| 2003/0195549 A1 | | 10/2003 | Davison et al. |
| 2003/0195550 A1 | | 10/2003 | Davison et al. |
| 2003/0195551 A1 | | 10/2003 | Davison et al. |
| 2003/0199871 A1 | | 10/2003 | Foley et al. |
| 2003/0199885 A1 | | 10/2003 | Davison et al. |
| 2003/0236529 A1 | | 12/2003 | Shluzas et al. |
| 2004/0059339 A1 | | 3/2004 | Roehm, III et al. |
| 2004/0078051 A1 | | 4/2004 | Davison et al. |
| 2004/0082960 A1 | | 4/2004 | Davison |
| 2004/0093002 A1 | | 5/2004 | Davison et al. |
| 2004/0097907 A1 | | 5/2004 | DiPoto |
| 2004/0098012 A1 | | 5/2004 | Davison et al. |
| 2004/0116954 A1 | | 6/2004 | Pagliuca et al. |
| 2004/0133201 A1 | | 7/2004 | Shluzas et al. |
| 2004/0236317 A1 | | 11/2004 | Davison |
| 2005/0021030 A1 | | 1/2005 | Pagliuca et al. |
| 2005/0033297 A1 | | 2/2005 | Davison |

| | | | |
|---|---|---|---|
| 2005/0075540 | A1 | 4/2005 | Shluzas et al. |
| 2005/0113833 | A1 | 5/2005 | Davison |
| 2006/0089662 | A1 | 4/2006 | Davison et al. |
| 2006/0264999 | A1 | 11/2006 | Davison et al. |
| 2006/0276821 | A1 | 12/2006 | Davison et al. |
| 2006/0276822 | A1 | 12/2006 | Davison et al. |

FOREIGN PATENT DOCUMENTS

| | | |
|---|---|---|
| EP | 0 528 562 A2 | 2/1993 |
| EP | 0 807 415 A2 | 11/1997 |
| EP | 0 807 415 A3 | 8/1998 |
| EP | 0 980 677 A1 | 2/2000 |
| EP | 1 251 767 A2 | 10/2002 |
| EP | 1 305 077 A1 | 5/2003 |
| FR | 2 701 379 A1 | 8/1994 |
| JP | 2000-83960 A2 | 3/2000 |
| JP | 2001-149376 A2 | 6/2001 |
| WO | WO 92/21292 A2 | 12/1992 |
| WO | WO 93/14801 A1 | 8/1993 |
| WO | WO 94/03114 A1 | 2/1994 |
| WO | WO 95/10218 A1 | 4/1995 |
| WO | WO 95/22285 A1 | 8/1995 |
| WO | WO 95/32663 A1 | 12/1995 |
| WO | WO 01/54560 A2 | 8/2001 |
| WO | WO 01/54560 A3 | 8/2001 |
| WO | WO 02/09801 A1 | 2/2002 |
| WO | WO 02/078767 A2 | 10/2002 |
| WO | WO 03/007783 A3 | 1/2003 |

OTHER PUBLICATIONS

"Arthroscopic Techniques for Spinal Surgery" by Kambin, Operative Arthroscopy, Second Edition, pp. 1215-1225 (1996).
"Diagnostic and Therapeutic Spinal Arthroscopy" by Kambin, Neurosurgery Clinics of North America, vol. 7, No. 1, pp. 65-76 (Jan. 1996).
"The Role of Minimally Invasive Surgery in Spinal Disorders" by Kambin, Advances in Operative Orthopedics, vol. 3, pp. 147-171 (1995).
"Arthroscopic Microdiskectomy" by Kambin, Mount Sinai J. of Medicine, pp. 159-164 (Mar. 1991).
Ditsworth, David A., M.D., *Surg Neurol*, 49; 588-598, 1998 "Endoscopic Transforaminal Lumbar Discectomy and Reconfiguration: A Postero-lateral Approach into the Spinal Canal".
Endius Marketing Bulletin, 2002, Atavi Atraumatic Spine Fusion System, "How do I decompress using Atavi System?"
Endius Marketing Bulletin, 2002, Atavi Atraumatic Spine Fusion System "Minimally Invasive Update on Danek".
Foley, Kevin T., M.D., Gupta, Sanjay K., M.D., Justis, Jeff R., B.S., Sherman, Michael C., M.S., *Neurosurg Focus*, 10: 1-8, 2001 "Percutaneous pedicle screw fixation of the lumbar spine".
Guiot, Bernard H., M.D., Khoo, Larry T., M.D., Fessler, Richard G., M.D., Ph.D., *Spine*, 27, 4: 432-438, 2002 "A Minimally Invasive Technique for Decompression of the Lumbar Spine".
Kambin, Parviz, Publisher Unknown, Chapter 77:1055-1066, Date Unknown "Arthroscopic Lumbar Interbody Fusion".
Medtronic Sofamor Danek, *METRx MicroEndoscopic Discectomy*, 1999 "An Evolution in Minimally Invasive Spine Surgery".
Medtronic Sofamor Danek, *METRx MicroDiscectomy System*, 2000 "The Next Step in Minimally Invasive Discectomy Utilizing The Operating Microscope".
Medtronic Sofmor Danek, *METRx Microdiscectomy Surgical Technique*, 2001 as described by: Donald L. Hilton, Jr., M.D., F.A.C.S. and Sylvain Palmer, M.D., F.A.C.S.
Medtronic Sofamor Danek, *Orthopedics Today*, 1-20, 2002 "Minimal Access Spinal Technologies".
Stauber, Martin H., M.D., Bassett, George S., M.D., *Spine*, 19, 1: 57-61, 1994 Pedicle Screw Placement With Intraosseous Endoscopy.
"Arthroscopic Fusion of the Lumbosacral Spine", Parviz Kambin, MD and Jonathan L. Schaffer, MD, Lumbosacral and Spinopelvic Fixation, 44:565-577, 1996.
"Posterolateral Percutaneous Lumbar Interbory Fusion", Parviz Kambin, Publisher Unknown, Chapter 9:117-121, Date Unknown.
Amendment to U.S. Appl. No. 10/439,979, filed May 16, 2003, dated Apr. 14, 2005; Notice of Allowance dated Jan. 14, 2005; Response to Office Action dated Oct. 5, 2004.
Amendment to U.S. Appl. No. 10/686,063, filed Oct. 15, 2003, dated Mar. 31, 2005.
MicroEndoscopic Discectomy System by Sofamor Danek USA, A manual entitled "MED™", pp. 1-33, 1996.
"The Caspar Microsurgical Discectomy and Comparison with a Conventional Standard Lumbar Disc Procedure" by Wolfhard Caspar et al., Neurosurgery vol. 28, No. 1, pp. 78-87, 1991.
U.S. Appl. No. 11/417,659, filed May 3, 2006, Davison et al.
Kambin, "Arthroscopic Microdiscectomy," The Adult Spine: Principles and Practice, 94: 2023-2036, 1997.

* cited by examiner

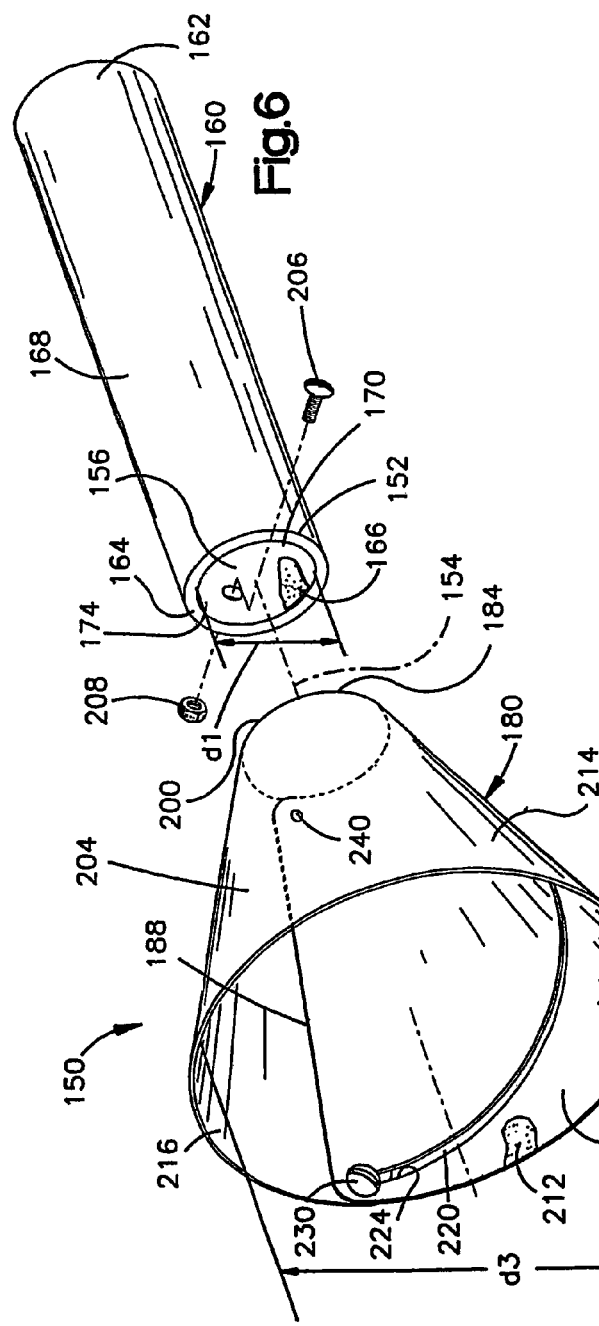
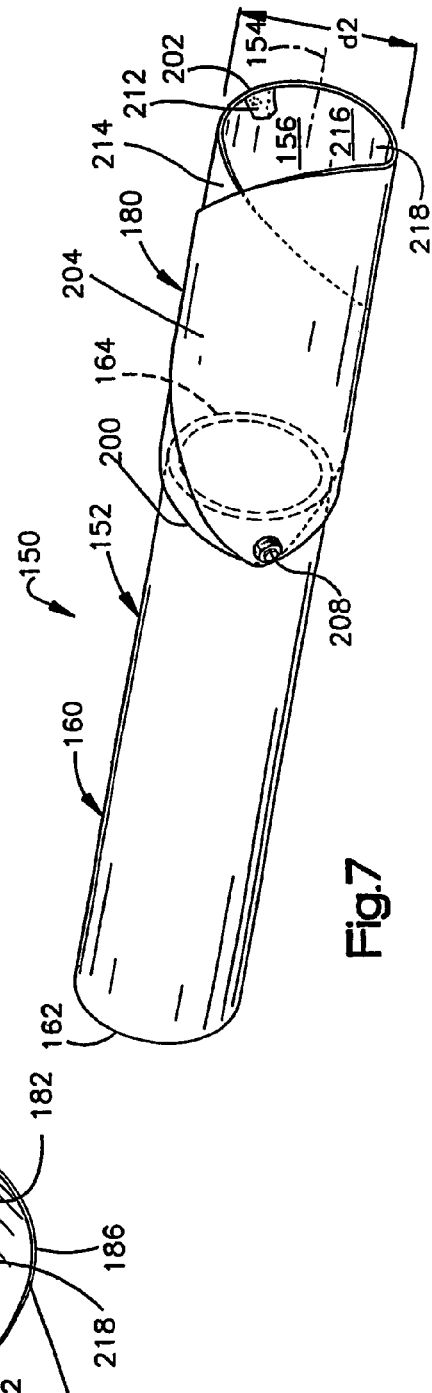

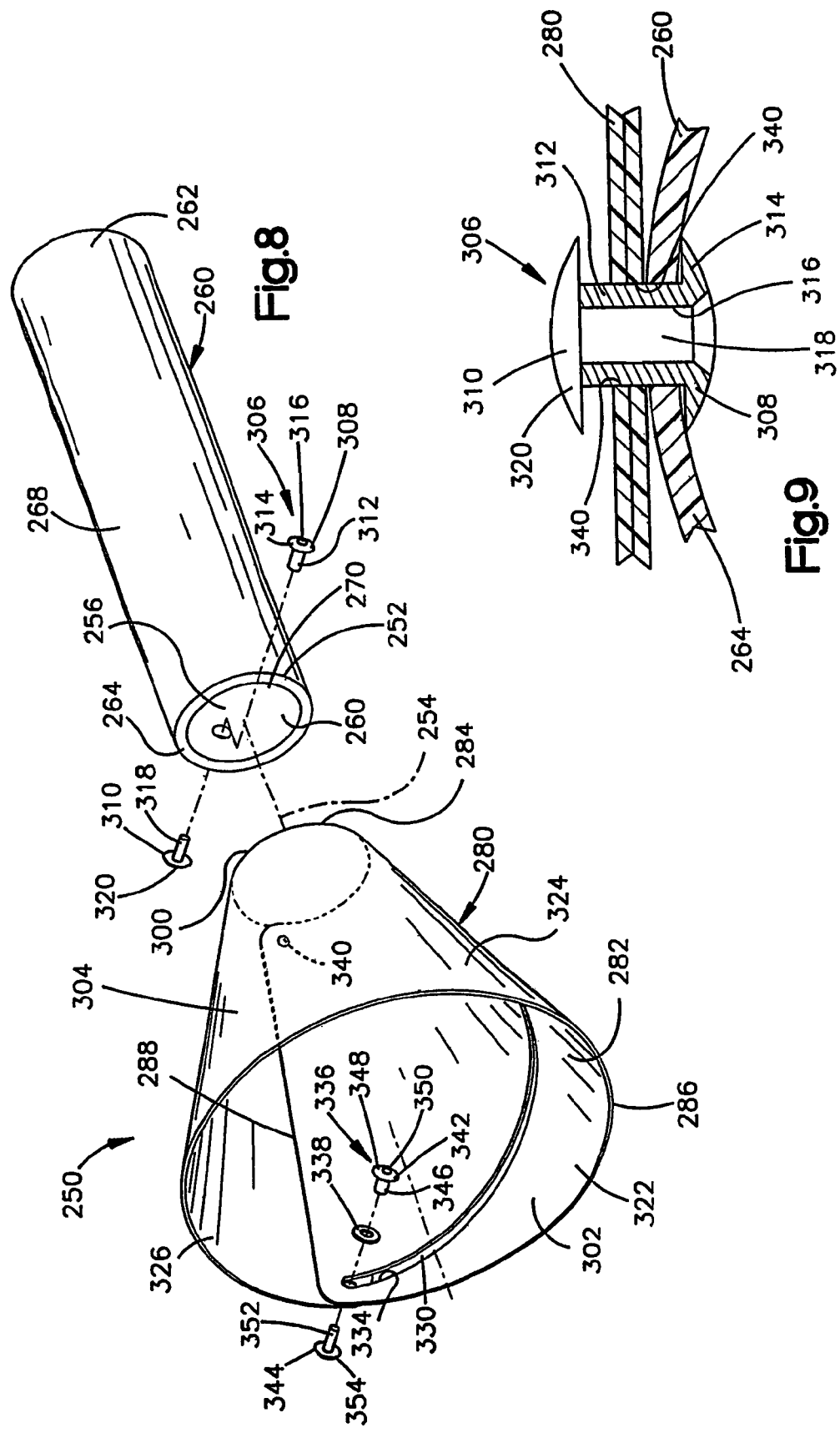

US 7,674,273 B2

METHOD FOR PERFORMING A SURGICAL PROCEDURE AND A CANNULA FOR USE IN PERFORMING THE SURGICAL PROCEDURE

This application is a divisional application of U.S. patent application Ser. No. 10/435,730, filed May 9, 2003 now U.S. Pat. No. 6,811,588,which is a divisional application of U.S. patent application Ser. No. 09/772,605, filed Jan. 30, 2001 now U.S. Pat. No. 6,800,084, which is a continuation-in-part of U.S. patent application Ser. No. 09/137,335, filed Aug. 20, 1998, now U.S. Pat. No. 6,187,000, issued Feb. 13, 2001.

TECHNICAL FIELD

The present invention is directed to a method for performing a surgical procedure on a body and a cannula for receiving surgical instruments during the surgical procedure.

BACKGROUND OF THE INVENTION

Endoscopic surgical techniques allow a surgical procedure to be performed on a patient's body through a relatively small incision in the body and with a limited amount of body tissue disruption. Endoscopic surgery typically utilizes a tubular structure known as a cannula which is inserted into a small incision in the body. The cannula holds the incision open and serves as a conduit extending between the exterior of the body and the local area inside the body where the surgery is to be performed.

Due to the relatively small size of the passage into the body which is defined by the cannula, certain surgical procedures, such as posterior disectomies and procedures using steerable surgical instruments, have been difficult to perform using endoscopic techniques.

SUMMARY OF THE INVENTION

The present invention is a method for performing a surgical procedure on a body and a cannula for receiving surgical instruments during the surgical procedure. In one embodiment, the method of performing the surgical procedure on the body includes providing the cannula having a tubular structure with first and second tubular portions defining first and second passages for receiving surgical instruments. The second passage is a continuation of the first passage.

The cannula is inserted through an incision in the body. The second tubular portion is inserted inside the body and the first tubular portion is inserted into the incision so that the first tubular portion extends from an exterior of the body to inside the body. The second tubular portion of the cannula expands to increase the cross-sectional area of the second passage in the second tubular portion while the second tubular portion is inside the body. The cross-sectional area of the first passage in the first tubular portion is maintained.

The first tubular portion of the cannula has a first thickness measured in a direction perpendicular to inner and outer surfaces of the first tubular portion. The second tubular portion has a thickness measured in a direction perpendicular to inner and outer surfaces of the second tubular portion. The first thickness is different than the second thickness.

BRIEF DESCRIPTION OF THE DRAWINGS

The foregoing and other features of the present invention will become apparent to one skilled in the art to which the present invention relates upon consideration of the following description of the invention with reference to the accompanying drawings, wherein:

FIG. 6 is a perspective view of a part of a surgical cannula constructed in accordance with a second embodiment of the present invention, the cannula being shown in an expanded condition;

FIG. 7 is a perspective view of the part of the cannula of FIG. 6, the cannula being shown in a contracted condition;

FIG. 8 is a perspective view of a part of a surgical cannula constructed in accordance with a third embodiment of the present invention, the cannula being shown in an expanded condition; and FIG. 9 is a sectional view of a portion of the cannula of FIG. 8 showing a rivet connecting a first tubular portion to a second tubular portion.

DESCRIPTION OF THE INVENTION

The present invention is directed to a method for performing a surgical procedure on the body of a patient and a cannula for receiving surgical instruments during the surgical procedure. The present invention is applicable to a variety of surgical procedures in which endoscopic surgical techniques are used.

Figure 1:
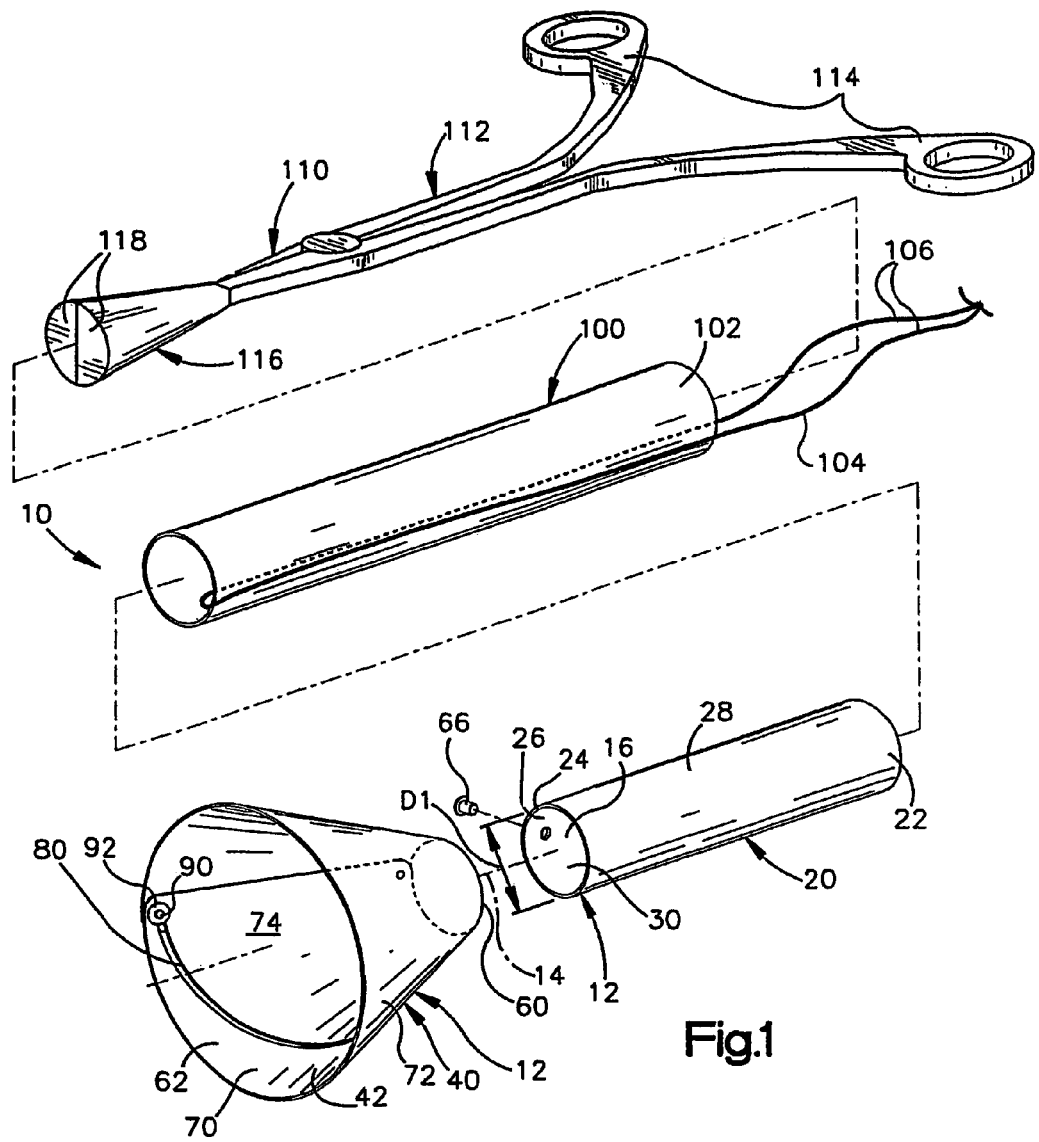
FIG. 1 is an exploded perspective view of a surgical cannula constructed in accordance with a first embodiment of the present invention, the cannula being shown in an expanded condition.

FIG. 1 illustrates a cannula 10 constructed according to a first embodiment of the present invention. The cannula 10 is a tubular structure 12 centered on an axis 14. The tubular structure 12 defines a passage 16 through the cannula 10. Surgical instruments are inserted into the body during endoscopic surgery through the passage 16.

The tubular structure 12 comprises a first tubular portion 20 and a second tubular portion 40 attached to the first tubular portion. The first tubular portion 20 is preferably made of a length of stainless steel tubing, but could alternatively be made of another suitable material such as a radiolucent material. The first tubular portion 20 has a proximal end 22 and a distal end 24. Parallel cylindrical inner and outer surfaces 26 and 28, respectively, extend between the ends 22, 24 of the first tubular portion 20. The inner surface 26 defines a first passage portion 30 of the passage 16 through the cannula 10. The first passage portion 30 has a diameter D1 which is preferably in the range from 10 mm to 20 mm or approximately 0.4 inches to approximately 0.8 inches.

The second tubular portion 40 of the tubular structure 12 is attached to the distal end 24 of the first tubular portion 20. The second tubular portion is preferably made from stainless steel, but could alternatively be made from another suitable material such as a radiolucent material.

Figure 4:
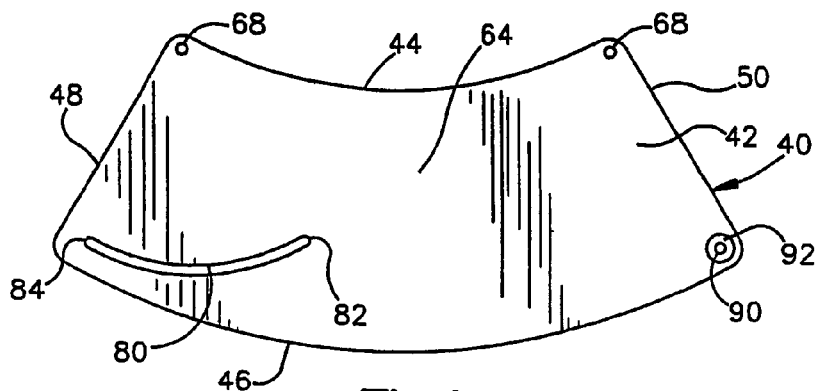
FIG. 4 is a rollout view of a part of the cannula of FIG. 1.

As best seen in the rollout view of FIG. 4, the second tubular portion 40 comprises an arcuate segment 42 of sheet stock. The arcuate segment 42 includes first and second arcuate edges 44 and 46, respectively, and first and second planar edges 48 and 50, respectively. The first and second planar edges 48 and 50 are rolled in an overlapping manner to form the tubular configuration of the second tubular portion 40.

When the second tubular portion 40 has been rolled into its tubular configuration, the first and second arcuate edges 44 and 46 define oppositely disposed first and second ends 60 and 62 (FIGS. 1 and 2), respectively, of the second tubular portion. The first and second ends 60 and 62 are connected by a central portion 64. The first end 60 of the second tubular portion 40 is attached to the distal end 24 of the first tubular portion 20 by a single suitable fastener, such as a rivet 66. The rivet 66 extends through two aligned apertures 68 (FIG. 4) at the first end 60 of the second tubular portion 40. The first end 60 of the second tubular portion 40 is pivotable about the rivet 66.

The second tubular portion 40 includes parallel inner and outer surfaces 70 and 72 (FIGS. 1 and 2), respectively, extending between the first and second ends 60 and 62. The inner surface 70 defines a second passage portion 74 of the passage 16 through the cannula 10 which extends as a continuation of the first passage portion 30 in the first tubular portion 20.

An arcuate slot 80 is formed in the second tubular portion 40 and extends between the inner and outer surfaces 70 and 72 of the second tubular portion. The arcuate slot 80 extends along a curvilinear path in the central portion 64 of the second tubular portion 40 toward the second end 60 of the second tubular portion. The arcuate slot 80 has a first terminal end 82 located in the central portion 64 of the second tubular portion 40. A second terminal end 84 of the arcuate slot 80 is located adjacent the intersection of the second arcuate edge 46 and the first planar edge 48 of the arcuate segment 42.

A suitable guide member, such as guide pin 90, is attached to the inner surface 70 of the second tubular portion 40 adjacent the intersection of the second arcuate edge 46 and the second planar edge 50. In the tubular configuration of the second tubular portion 40, the guide pin 90 is located in the arcuate slot 80 and is movable along the curvilinear path of the arcuate slot. A washer 92 is secured to an inner end of the guide pin 90 to retain the guide pin in the arcuate slot 80.

Figure 2:
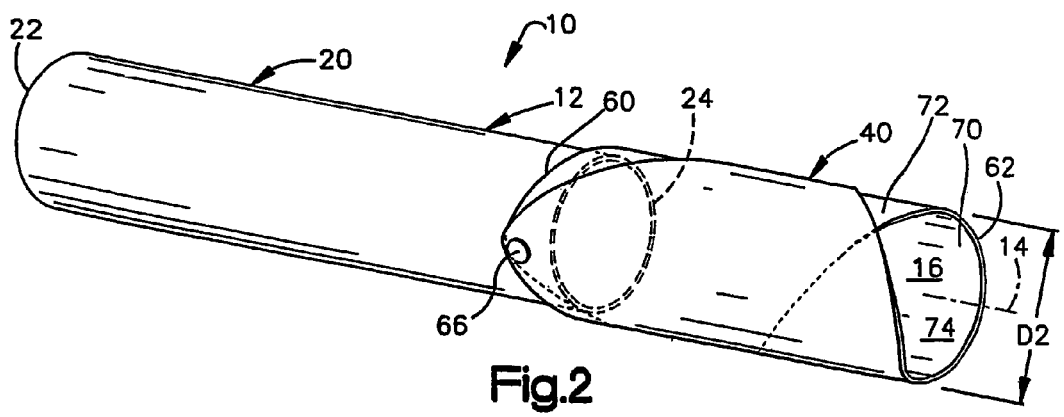
FIG. 2 is a perspective view of the cannula of FIG. 1 with parts removed for clarity, the cannula being shown in a contracted condition.
Figure 3:
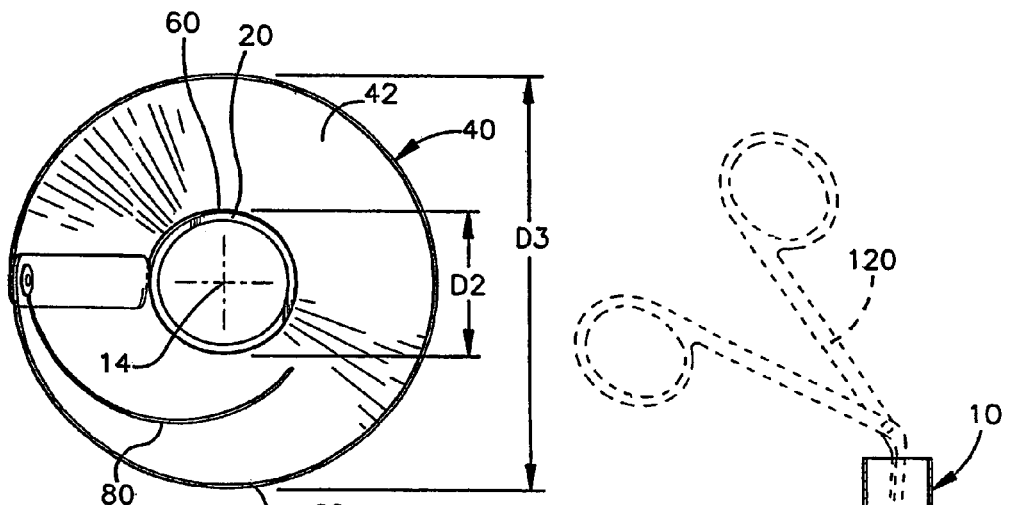
FIG. 3 is a schematic end view showing the cannula of FIG. 1 in the expanded position.

The second tubular portion 40 of the tubular structure 12 is expandable from a contracted condition shown in FIG. 2 to an expanded-condition shown in FIG. 1. In the contracted condition, the guide pin 90 is located in the first terminal end 82 of the arcuate slot 80 in the second tubular portion 40 and the second passage portion 74 defined by the second tubular portion is cylindrical in shape. The second passage 74 has a generally constant diameter D2 (FIGS. 2 and 3) which is approximately equal to the diameter D1 of the first tubular portion 20. Thus, the cross-sectional area of the second passage portion 74 at the second end 62 of the second tubular portion 40, which is a function of the diameter D2, is approximately the same as the cross-sectional area at the first end 60 of the second tubular portion and is approximately the same as the cross-sectional area of the first passage portion 30 in the first tubular portion 20.

In the expanded condition, the guide pin 90 is located in the second terminal end 84 of the arcuate slot 80 in the second tubular portion 40 and the second tubular portion has a conical configuration. At the second end 62 of the second tubular portion 40, the second passage portion 74 has a diameter D3 (FIG. 3) which is larger than the diameter D2 of the second passage portion at the first end 60. Preferably, the diameter D3 of the second passage portion 74 at the second end 62 of the second tubular portion 40 is 40% to 80% greater than the diameter D2 of the second passage portion at the first end 60. Thus, in the expanded condition, the cross-sectional area of the second passage portion 74 at the second end 62 of the second tubular portion 40, which is a function of the diameter D3, is greater than the cross-sectional area of the second passage portion at the first end 60 of the second tubular portion.

The cannula 10 includes an outer layer 100 (FIG. 1) for maintaining the second tubular portion 40 of the cannula in the contracted condition. It is contemplated that other suitable means for maintaining the second tubular portion 40 in the contracted condition could be employed. In accordance with a preferred embodiment of the present invention, the outer layer 10 comprises a section of plastic tubing 102 which is heat shrunk over both the first and second tubular portions 20 and 40 to hold the second tubular portion in the contracted condition.

In addition, a loop of nylon string 104 for tearing the heat shrink tubing 102 is wrapped around the heat shrink tubing so that it extends both underneath and on top of the tubing. An outer end 106 of the string 104 extends beyond the tubing 102.

The cannula 10 further includes an actuatable device 110 for expanding the second tubular portion 40 from the contracted condition to the expanded condition. In accordance with a preferred embodiment of the present invention, the actuatable device 110 comprises a manually operated expansion tool 112. The expansion tool 112 resembles a common pair of scissors and has a pair of legs 114 pivotally connected to one another. The expansion tool 112 includes a frustoconical end section 116 formed by a pair of frustoconical halves 118. Each of the frustoconical halves 118 extends from a respective one of the legs 114 of the expansion tool 112. It is contemplated that other suitable means for expanding the second tubular portion 40 toward the expanded condition could be employed, such as an inflatable balloon (not shown).

During an endoscopic surgical procedure, the cannula 10 is inserted in the contracted condition through an incision into the body of a patient. The second tubular portion 40 is inserted inside the body. The first tubular portion 20 is inserted into the incision so that the first tubular portion extends from an exterior of the body to inside the body.

The outer end 106 of the string 104 is then manually pulled on by the surgeon. Pulling on the string 104 tears the heat shrink tubing 102 which is then removed from the cannula 10 by the surgeon. With the heat shrink tubing 102 removed, the second tubular portion 40 of the cannula 10 is thereby released for expansion toward the expanded condition.

Next, the expansion tool 112 is inserted into the passage 16 in the cannula 10 until the frustoconical end section 114 is located at the second end 62 of the second tubular portion 40. The legs 114 of the expansion tool 112 are manually separated, causing the frustoconical halves 118 to separate also. As the halves 118 separate, a radially outwardly directed force is exerted on the inner surface 70 of the second tubular portion 40 by the halves 118, causing the second tubular portion to expand toward the expanded condition.

Figure 5:
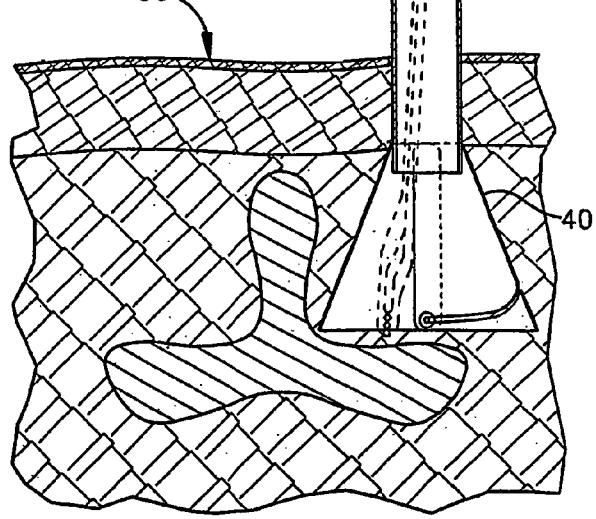
FIG. 5 is a schematic sectional view of the cannula of FIG. 1 during a surgical procedure.

Under the force of the expanding expansion tool 112, the guide pin 90 slides from the first terminal end 82 of the arcuate slot 80 to the second terminal end 84 of the arcuate slot to permit the expansion of the second tubular portion 40. The expansion tool 112 can be rotated about the axis 14 to ensure that the second tubular portion 40 of the cannula 10 is completely expanded to the expanded condition. The expansion tool 112 is then collapsed and removed so that one or more surgical instruments (indicated schematically at 120 in FIG. 5) can be received through the cannula 10 and inserted into a patient's body 130.

The expandable second tubular portion 40 of the cannula 10 provides a significantly larger working area for the surgeon inside the body 130 within the confines of the cannula. As a result, the simultaneous use of a number of endoscopic surgical instruments, including but not limited to steerable instruments, shavers, dissectors, scissors, forceps, retractors, dilators, and video cameras, is made possible by the expandable cannula 10.

A cannula 150 constructed according to a second embodiment of the present invention is illustrated in FIGS. 6-7. The cannula 150 includes a tubular structure 152 centered on an axis 154. The tubular structure 152 defines a passage 156 through the cannula 150. Surgical instruments are inserted into the body during endoscopic surgery through the passage 156.

The tubular structure 152 (FIG. 6) comprises a first tubular portion 160 and a second tubular portion 180 attached to the first tubular portion. The first tubular portion 160 is preferably made of a length of stainless steel tubing, but could alternatively be made of another suitable material, such as a radiolucent material. The first tubular portion 160 has a proximal end 162 and a distal end 164. Parallel cylindrical inner and outer surfaces 166 and 168 extend between the ends 162, 164 of the first tubular portion 160. The first tubular portion 160 has a thickness measured perpendicular to the surfaces 166 and 168 in the range of 0.02 inches to 0.04 inches or approximately 0.5 mm to approximately 1.0 mm.

The inner surface 166 defines a first passage portion 170 of the passage 156 through the cannula 150. The first passage portion 170 has a diameter d1 which is preferably in the range from 10 mm to 20 mm or approximately 0.4 inches to approximately 0.8 inches. The inner surface 166 has a non-reflective coating 174. The non-reflective coating 174 reduces glare on any video image produced by a video camera inserted through the passage 156. It is contemplated that the inner surface 166 may not have the coating 174.

The second tubular portion 180 (FIG. 6) of the tubular structure 152 is attached to the distal end 164 of the first tubular portion 160. The second tubular portion 180 is preferably made from stainless steel, but could alternatively be made from another suitable material, such as a radiolucent material.

The second tubular portion 180 includes an arcuate segment 182 of sheet stock. The arcuate segment 182 includes first and second arcuate edges 184 and 186. The arcuate segment 182 also includes a first planar edge 188 and a second planar edge extending between the arcuate edges 184 and 186, which is not shown in FIG. 6. The first and second planar edges are rolled in an overlapping manner to form the tubular configuration of the second tubular portion 180. When the second tubular portion 180 has been rolled into its tubular configuration, the first and second arcuate edges 184 and 186 define oppositely disposed first and second ends 200 and 202 of the second tubular portion. The first and second ends 200 and 202 are connected by a central portion 204. The first end 200 of the second tubular portion 180 is attached to the distal end 164 of the first tubular portion 160 by a suitable fastener, such as a screw 206 and nut 208 threaded on the screw. It is contemplated that the second tubular portion 180 could be connected to the first tubular portion 160 by a rivet. The screw 206 extends through two aligned apertures 240 at the first end 200 of the second tubular portion 180. The first end 200 of the second tubular portion 180 is pivotable about the screw 206.

The second tubular portion 180 includes parallel inner and outer surfaces 212 and 214 extending between the first and second ends 200 and 202. The inner surface 212 defines a second passage portion 216 of the passage 156 through the cannula 150 which extends as a continuation of the first passage portion 17.0 in the first tubular portion 160. The second tubular portion 180 has a thickness measured perpendicular to the surfaces 212 and 214 in the range of 0.003 inches to 0.005 inches or approximately 0.075 mm to approximately 0.125 mm. The inner surface 212 has a non-reflective coating 218. The non-reflective coating 218 reduces glare on any video image produced by a camera inserted through the passage 156. It is contemplated that the inner surface 212 may not have the coating 218.

An arcuate slot 220. (FIG. 6) is formed in the second tubular portion 180 and extends between the inner and outer surfaces 212 and 214 of the second tubular portion. The arcuate slot 220 extends along a curvilinear path in the central portion 204 of the second tubular portion 180 toward the end 184 of the second tubular portion. The arcuate slot 220 has a first terminal end (not shown) located in the central portion 204 of the second tubular portion 180. A second terminal end 224 of the arcuate slot 220 is located adjacent the intersection of the second arcuate edge 186 and the planar edge 188 of the arcuate segment 182.

A guide member or screw 230 is attached to the inner surface 212 of the second tubular portion 180 adjacent the intersection of the second arcuate edge 186 and the planar edge (not shown). It is contemplated that a guide pin could be used instead of the screw 230. In the tubular configuration of the second tubular portion 180, the guide member 230 is located in the arcuate slot 220 and is movable along the curvilinear path of the arcuate slot.

The second tubular portion 180 of the tubular structure 152 is expandable from a contracted condition, shown in FIG. 7, to an expanded condition, shown in FIG. 6. In the contracted condition (FIG. 7), the guide member 230 is located in the first terminal end (not shown) of the arcuate slot 220 in the second tubular portion 180 and the second passage portion 216 defined by the second tubular portion is cylindrical in shape. The second passage 216 has a generally constant diameter d2 which is approximately equal to the diameter d1 of the first tubular portion 160. Thus, the cross-sectional area of the second passage portion 216 at the second end 202 of the second tubular portion 180, which is a function of the diameter d2, is approximately the same as the cross-sectional area at the first end 200 of the second tubular portion and is approximately the same as the cross-sectional area of the first passage portion 170 in the first tubular portion 160.

In the expanded condition (FIG. 6), the guide member 230 is located in the second terminal end 224 of the arcuate slot 220 in the second tubular portion 180 and the second tubular portion has a conical configuration. At the second end 202 of the second tubular portion 180, the second passage portion 216 has a diameter d3 which is larger than the diameter d2 of the second passage portion at the first end 200. Preferably, the diameter d3 of the second passage portion 216 at the second end 202 of the second tubular portion 180 is 40% to 80% greater than the diameter d2 of the second passage portion at the first end 200. Thus, in the expanded condition, the cross-sectional area of the second passage portion 216 at the second end 202 of the second tubular portion 180, which is function of the diameter d3, is greater than the cross-sectional area of the second passage portion at the first end 200 of the second tubular portion.

The cannula 150 includes an outer member (not shown) for maintaining the second tubular portion 180 of the cannula in the contracted condition. It is contemplated that other suitable means for maintaining the second tubular portion 180 in the contracted condition could be employed. In accordance with the present invention, the outer member may be similar to the layer 100 shown in FIG. 1 and include a section of plastic tubing which is heat shrunk over both the first and second tubular portions 160 and 180 to hold the second tubular portion in the contracted condition. In addition, a loop of nylon string (not shown) for tearing the heat shrink tubing is wrapped around the heat shrink tubing so that it extends both underneath and on top of the tubing. An outer end of the string extends beyond the tubing.

During an endoscopic surgical procedure, the cannula 150 is inserted in the contracted condition through an incision into the body of a patient. The second tubular portion 180 is inserted inside the body. The first tubular portion 160 is inserted into the incision so that the first tubular portion extends from an exterior of the body to inside the body.

The outer end of the string is then manually pulled on by the surgeon. Pulling on the string tears the heat shrink tubing which is then removed from the cannula 150 by the surgeon. With the heat shrink tubing removed, the second tubular portion 180 of the cannula 150 is thereby released for expansion toward the expanded condition.

Next, the expansion tool 112, shown in FIG. 1, is inserted into the passage 156 in the cannula 150 until the frustoconical end section 114 is located at the second end 202 of the second tubular portion 180. The legs 114 of the expansion tool 112 are manually separated, causing the frustoconical halves 118 to separate also. As the halves 118 separate, a radially outwardly directed force is exerted on the inner surface 212 of the second tubular portion 180 by the halves 118, causing the second tubular portion to expand toward the expanded condition. Under the force of the expanding expansion tool 112, the guide member 230 slides from the first terminal end of the arcuate slot 220 to the second terminal end of the arcuate slot to permit the expansion of the second tubular portion 180. The expansion tool 112 can be rotated about the axis 154 to ensure that the second tubular portion 180 of the cannula 150 is completely expanded to the expanded condition. The expansion tool 112 is then collapsed and removed so that one or more surgical instruments can be received through the cannula 150 and inserted into a patient's body.

The thickness of the second tubular portion 180 allows the second tubular portion to deform as the second tubular portion expands. As the second tubular portion 180 expands and engages tissue in the body, the tissue resists expansion of the second tubular portion. The second tubular portion 180 must deform slightly to prevent the second tubular portion from being damaged while expanding.

The expandable second tubular portion 180 of the cannula 150 provides a significantly larger working area for the surgeon inside the body within the confines of the cannula. As a result, the simultaneous use of a number of endoscopic surgical instruments, including but not limited to steerable instruments, shavers, dissectors, scissors, forceps, retractors, dilators, and video cameras, is made possible by the expandable cannula 150.

A cannula 250 constructed according to a third embodiment of the present invention is illustrated in FIGS. 8-9. In the embodiment of the invention illustrated in FIGS. 6-7 the tubular portions 160 and 180 are connected by a screw 206 and nut 208 and the guide member is a screw 230. In the embodiment of the invention illustrated in FIGS. 8-9 the tubular portions are connected by a rivet and the guide member is a rivet. The cannula 250 is generally similar to the cannula 150 shown in FIGS. 6-7. Accordingly, only the rivets will be described in detail.

The cannula 250 (FIG. 8) includes a tubular structure 252 centered on an axis 254. The tubular structure 252 defines a passage 256 through the cannula 250. The tubular structure 252 includes a first tubular portion 260 and a second tubular portion 280 attached to the first tubular portion. The first tubular portion 260 has a proximal end 262 and a distal end 264. Parallel cylindrical inner and outer surfaces 266 and 268 extend between the ends 262, 264 of the first tubular portion 260. The inner surface 266 defines a first passage portion 270 of the passage 256 through the cannula 250. The inner surface 266 could have a non-reflective coating (not shown).

The second tubular portion 280 (FIG. 8) of the tubular structure 252 is attached to the distal end 264 of the first tubular portion 260. The second tubular portion 280 includes an arcuate segment 282 of sheet stock. The arcuate segment 282 includes first and second arcuate edges 284 and 286. The arcuate segment 282 also includes a first planar edge 288 and a second planar edge extending between the arcuate edges 284 and 286, which is not shown in FIG. 8. The first and second planar edges are rolled in an overlapping manner to form the tubular configuration of the second tubular portion 280.

When the second tubular portion 280 has been rolled into its tubular configuration, the first and second arcuate edges 284 and 286 define oppositely disposed first and second ends 300 and 302 of the second tubular portion. The first and second ends 300 and 302 are connected by a central portion 304. The first end 300 of the second tubular portion 280 is attached to the distal end 264 of the first tubular portion 260 by a rivet 306. The rivet 306 extends through two aligned apertures 340 at the first end 300 of the second tubular portion 280. The first end 300 of the second tubular portion 280 is pivotable about the rivet 306.

The rivet 306 (FIGS. 8 and 9) has a first portion 308 and a second portion 310. The first portion 308 has a shaft 312 extending from a head 314. The shaft 312 extends through the apertures 340 in the tubular portion 280 and the head 314 engages the inner surface 266 of the first tubular portion 260. A cylindrical opening 316 extends through the shaft 312 and the head 314.

The second portion 310 of the rivet 306 has a shaft 318 extending from a head 320. The shaft 318 extends into the opening 316 in the first portion 308 of the rivet 306 and the head 320 engages the second tubular portion 280. The shaft 318 of the second portion 310 extends into the opening 316 in the first portion 308 to connect the first and second portions of the rivet 306 and pivotally-connect the second tubular portion 280 to the first tubular portion 260.

The second tubular portion 280 (FIG. 8) includes parallel inner and outer surfaces 322 and 324 extending between the first and second ends 300 and 302. The inner surface 322 defines a second passage portion 326 of the passage 256 through the cannula 250 which extends as a continuation of the first passage portion 270 in the first tubular portion 260. The inner surface 322 could have a non-reflective coating (not shown).

An arcuate slot 330 is formed in the second tubular portion 280 and extends between the inner and outer surfaces 322 and 324 of the second tubular portion. The arcuate slot 330 extends along a curvilinear path in the central portion 304 of the second tubular portion 280 toward the end 284 of the second tubular portion. The arcuate slot 330 has a first terminal end (not shown) located in the central portion 304 of the second tubular portion 280. A second terminal end 334 of the arcuate slot 330 is located adjacent the intersection of the second arcuate edge 286 and the planar edge 288 of the arcuate segment 282.

A rivet 336 is attached to the inner surface 322 of the second tubular portion 280 adjacent the intersection of the second arcuate edge 286 and the planar edge (not shown). It is contemplated that a guide pin could be used instead of the rivet 336. In the tubular configuration of the second tubular portion 280, the rivet 336 is located in the arcuate slot 330 and is movable along the curvilinear path of the arcuate slot. The rivet 336 extends through a washer 338 to retain the rivet in the arcuate slot 330.

The rivet 336 is generally similar to the rivet 306 and, therefore, will not be described in detail. The rivet 336 has a first portion 342 and a second portion 344. The first portion 342 has a shaft 346 extending from a head 348. The shaft 346 extends through the slot 330 and the head 348 engages the washer 338. A cylindrical opening 350 extends through the shaft 346 and the head 348.

The second portion 344 of the rivet 336 has a shaft 352 extending from a head 354. The shaft 352 extends into the opening 350 in the first portion 342 of the rivet 336 and the head 354 engages the outer surface 324 of the second tubular portion 280. The shaft 352 extends into the opening 350 to connect the first portion 342 of the rivet 336 to the second portion 344.

The second tubular portion 280 of the tubular structure 252 is expandable from a contracted condition to an expanded condition, shown in FIG. 8. In the contracted condition the rivet 336 is located in the first terminal end (not shown) of the arcuate slot 330 in the second tubular portion 280 and the second passage portion 326 defined by the second tubular portion is cylindrical in shape. The second passage portion 326 has a generally constant diameter which is approximately equal to the diameter of the first tubular portion 260. Thus, the cross-sectional area of the second passage portion 326 at the second end 302 of the second tubular portion 280 is approximately the same as the cross-sectional area at the first end 300 of the second tubular portion and is approximately the same as the cross-sectional area of the first passage portion 270 in the first tubular portion 260.

In the expanded condition (FIG. 8), the rivet 336 is located in the second terminal end 334 of the arcuate slot 330 in the second tubular portion 280 and the second tubular portion has a conical configuration. At the second end 302 of the second tubular portion 280, the second passage portion 326 has a diameter which is larger than the diameter of the second passage portion at the first end 300. Thus, in the expanded condition, the cross-sectional area of the second passage portion 326 at the second end 302 of the second tubular portion 280 is greater than the cross-sectional area of the second passage portion at the first end 300 of the second tubular portion.

During an endoscopic surgical procedure, the cannula 250 is inserted in the contracted condition through an incision into the body of a patient. The second tubular portion 280 is inserted inside the body. The first tubular portion 260 is inserted into the incision so that the first tubular portion extends from an exterior of the body to inside the body.

Heat shrink tubing is removed from the cannula 250 by the surgeon. With the heat shrink tubing removed, the second tubular portion 280 of the cannula 250 is thereby released for expansion toward the expanded condition. Next, the expansion tool 112, shown in FIG. 1, is inserted into the passage 256 in the cannula 250 until the frustoconical end section 114 is located at the second end 302 of the second tubular portion 280. The legs 114 of the expansion tool 112 are manually separated, causing the frustoconical halves 118 to separate also. As the halves 118 separate, a radially outwardly directed force is exerted on the inner surface 312 of the second tubular portion 280 by the halves 118, causing the second tubular portion to expand toward the expanded condition. Under the force of the expanding expansion tool 112, the rivet 336 slides from the first terminal end of the arcuate slot 330 to the second terminal end 334 of the arcuate slot to permit the expansion of the second tubular portion 280. The expansion tool 112 is then collapsed and removed so that one or more surgical instruments can be received through the cannula 250 and inserted into a patient's body. The expandable second tubular portion 280 of the cannula 250 provides a significantly larger working area for the surgeon inside the body within the confines of the cannula. As a result, the simultaneous use of a number of endoscopic surgical instruments including but not limited to steerable instruments, shavers, dissectors, scissors, forceps, retractors, dilators, and video cameras, is made possible by the expandable cannula 250.

It is contemplated that the cannula 10, 150, and/or the cannula 250 described herein could be the centerpiece of an endoscopic surgical kit which would include an assortment of surgical instruments designed and/or selected for use with the cannula.

From the above description of the invention, those skilled in the art will perceive improvements, changes and modifications. Such improvements, changes and modifications within the skill of the art are intended to be covered by the appended claims.

We claim:

1. A method for providing minimally invasive access to a spinal location of a patient, said method comprising:
   inserting an access device through the skin of a patient, the access device having a first access portion having a first outer surface and a first inner surface at least partially defining a passage for receiving a plurality of surgical instruments, the access device having a second access portion attached to said first access portion, the second access portion having a second outer surface and a second inner surface at least partially defining the passage for receiving at least one surgical instrument;
   positioning the access device in the patient such that a proximal portion thereof is outside the patient and a distal portion is near the spine;
   inserting an expander device into the access device;
   actuating the expander device to cause opposing portions of the distal portion of the access device to move in a direction generally transverse to a longitudinal axis of the passage, thereby moving the access device from a contracted condition to an expanded condition, causing the outer surface of the distal portion to retract the tissue surrounding the spine to provide a surgical field for the spinal surgical procedure;
   pivoting the proximal portion of the access device from a first position to a second position adapted to enhance the visibility and access of the surgical field; and
   inserting an instrument through the passage to perform a procedure on the spine.

2. The method of claim 1, wherein the first access portion comprises a portion of the proximal portion.

3. The method of claim 1, wherein the second access portion comprises a portion of the distal portion.

4. The method of claim 3, wherein the first access portion comprises a portion of the proximal portion.

5. The method of claim 4, wherein said access device further comprises a fastener and the pivoting is provided about said fastener.

6. The method of claim 5, wherein the first access portion comprises a first hole and the second access portion comprises a second hole, the fastener extending through the first hole and the second hole.

7. The method of claim 6, wherein the fastener comprises a rivet.

8. The method of claim 1, wherein the second access portion comprises an arcuate segment that is rolled such that first and second opposite ends overlap in an area where the first end extends over the second end.

9. The method of claim 8, wherein the overlap area is reduced by actuating the expander device.

10. The method of claim 9, wherein said access device further comprises a fastener and the pivoting is provided about said fastener.

11. The method of claim 10, wherein the first access portion comprises a first hole and the second access portion comprises a second hole, the fastener extending through the first hole and the second hole.

12. The method of claim 10, wherein the fastener comprises a rivet.

13. The method of claim 1, further comprising forming an incision in the skin of the patient and inserting the access device through the incision.

14. The method of claim 1, further comprising:
advancing a first surgical instrument through the passage to the spinal location; and
inserting a second surgical instrument into the passage while the first surgical instrument is in the passage.

15. The method of claim 1, wherein the passage has a width in the second access portion that is greater than about 14 mm.

16. The method of claim 1, wherein the passage has a width in the second access portion that is between about 14 mm and about 36 mm.

17. The method of claim 1, wherein actuating the expander device in the access device causes the second access portion to be shaped like a portion of a cone.

18. The method of claim 1, wherein the first access portion comprises a tubular portion.

19. The method of claim 18, wherein the second access portion is coupled with the tubular portion and extends distally therefrom.

20. The method of claim 1, wherein the cross-sectional area of a portion of the passage in the distal portion is approximately constant before and after actuating the expander tool.

21. The method of claim 1, wherein the access device further comprises a first edge and a second edge, the first edge and second edge cooperating to limit movement of the distal portion of the access device.

22. The method of claim 21, wherein the access device comprises an arcuate slot and a guide member disposed in said arcuate slot, the first edge defining an edge of the slot and the second edge defining a portion of the guide member.

23. A method for providing minimally invasive access to a spinal location of a patient, said method comprising:
inserting an access device through the skin of a patient, the access device having a first access portion having a first outer surface and a first inner surface at least partially defining a passage for receiving a plurality of surgical instruments, the access device having a second access portion attached to said first access portion, the second access portion formed of an arcuate segment of sheet stock having first and second opposite ends, the sheet rolled into a tubular shape with overlapping first and second ends, the sheet having a second outer surface and a second inner surface at least partially defining the passage for receiving at least one surgical instrument;
inserting the access device through an incision in the patient such that a proximal portion thereof is outside the patient and a distal portion is near the spine; inserting an expander device into the access device
actuating the expander device to cause opposing portions of the distal portion of the access device to moved in a direction generally transverse to a longitudinal axis of the passage, thereby moving the access device from a contracted condition to an expanded condition causing the outer surface of the distal portion to retract the tissue surrounding the spine to provide a surgical field for the spinal surgical procedure;
pivoting the proximal portion of the access device from a first position to a second position adapted to enhance the visibility and access of the surgical field; and
inserting an instrument through the passage to perform a procedure on the spine.

24. A method for providing minimally invasive access to a spinal location of a patient, said method comprising:
inserting an access device through the skin of a patient, the access device having a first access portion having a first outer surface and a first inner surface at least partially defining a passage for receiving a plurality of surgical instruments, the access device having a second access portion attached to said first access portion, the second access portion having a second outer surface and a second inner surface at least partially defining the passage for receiving at least one surgical instrument, the second access portion having an arcuate slot and a guide member disposed in the arcuate slot;
positioning the access device in the patient such tat a proximal portion thereof is outside the patient and a distal portion is near the spine; inserting an expander device into the access device
actuating the expander device to cause the guide member of the access device to move from a first terminal end of the slot toward a second terminal end of the slot to move opposing portions of the distal portion of the access device in a direction generally transverse to a longitudinal axis of the passage, thereby moving the access device from a contracted condition to an expanded condition, thereby increasing a cross sectional area of the passage and causing the outer surface of the distal portion to retract the tissue surrounding the spine to provide a surgical field for the spinal surgical procedure;
pivoting the proximal portion of the access device from a first position to a second position adapted to enhance the visibility and access of the surgical field; and
inserting an instrument through the passage to perform a procedure on the spine.

* * * * *